US00PP30112P2

(12) United States Plant Patent
Van Dijk

(10) Patent No.: US PP30,112 P2
(45) Date of Patent: Jan. 15, 2019

(54) ***ANTHURIUM* PLANT NAMED 'ANTHFAXI'**

(50) Latin Name: ***Anthurium andraeanum* L.**
Varietal Denomination: ANTHFAXI

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/731,739

(22) Filed: Jul. 26, 2017

(51) Int. Cl.
*A01H 5/02* (2018.01)

(52) U.S. Cl.
USPC ..... Plt./369

(58) Field of Classification Search
USPC ..... Plt./365, 369
See application file for complete search history.

*Primary Examiner* — Keith O. Robinson
(74) *Attorney, Agent, or Firm* — Jondle & Associates, P.C.

(57) ABSTRACT

A new *Anthurium* plant named 'ANTHFAXI' particularly distinguished by having unique white, cordate spathes with red tips that retain the original color for a long period of time, dark green and ovate-cordate, durable leaves, red spadix with lighter red tips, early flowering continuously throughout the year and a plant height of 30.0 cm to 35.0 cm, is disclosed.

3 Drawing Sheets

Genus and species: *Anthurium andraeanum* L.
Variety denomination: 'ANTHFAXI'.

BACKGROUND OF THE NEW PLANT

The present invention comprises a new and distinct variety of *Anthurium*, botanically known as *Anthurium andraeanum* L., and hereinafter referred to by the variety name 'ANTHFAXI'. The new *Anthurium* plant is a product of a planned breeding program conducted by the inventor in Bleiswijk, the Netherlands. The objective of this breeding program was to create a new 30.0 cm to 35.0 cm height plant having unique white spathes with red tips.

The new variety originated from a cross-pollination made in September 2009 in Bleiswijk, The Netherlands. The female parent was a white with red tip *Anthurium* pot plant designated '16542-06' (unpatented), and the male parent was a light pink with red tip *Anthurium* pot plant designated '18376-08' (unpatented).

A single plant was selected from the progeny of the stated cross in October 2011 and has been asexually reproduced repeatedly by tissue culture in Bleiswijk, The Netherlands over a 6-year period. The present invention has been found to retain its distinctive characteristics through successive asexual propagations.

Plant Breeder's Rights for this variety have been applied for in the European Union on Nov. 24, 2015. 'ANTHFAXI' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Unique white spathe with red tip;
2) Red spadix with lighter red tip; and
3) Green, ovate-cordate leaves.

DESCRIPTION OF THE PHOTOGRAPHS

This new *Anthurium* plant is illustrated by the accompanying photographs which show the overall plant habit including blooms, bud and foliage of the plant; the colors shown are as true as can be reasonably obtained by conventional photographic procedures. The photographs are of a 44-week old plant grown in a greenhouse in Bleiswijk, The Netherlands in June 2017. Colors in the photographs may differ from the color values cited in the detailed botanical description, which accurately describe the actual colors of the new variety.

DESCRIPTION OF THE NEW VARIETY

Figure 1:
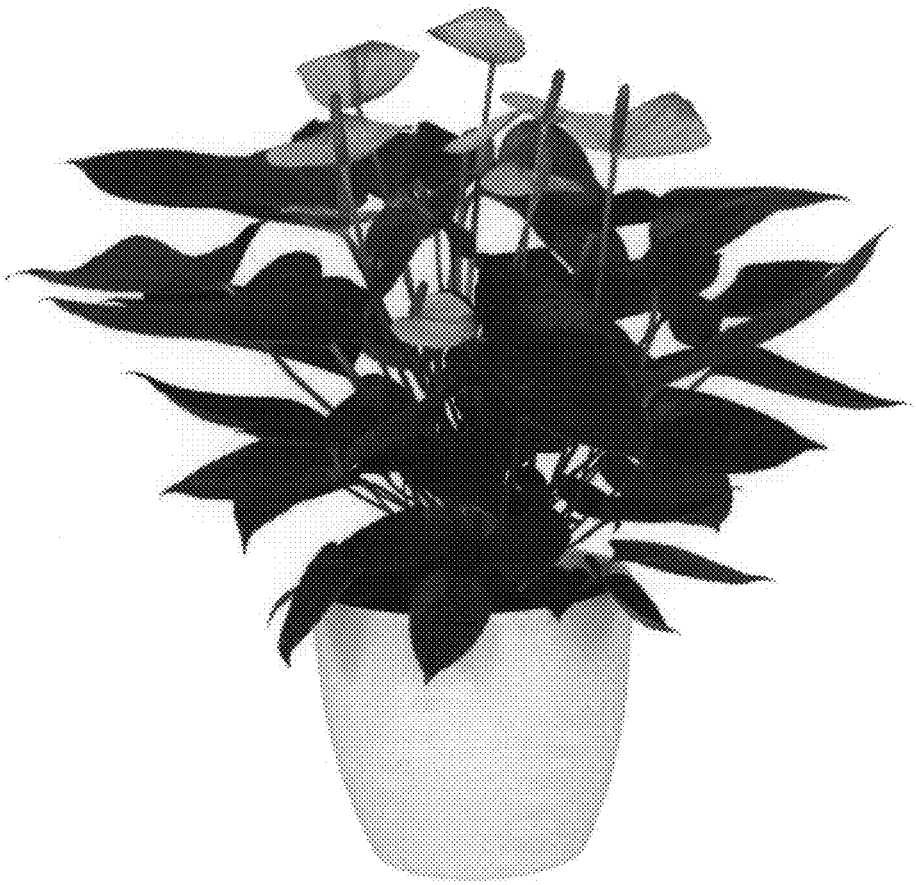
FIG. 1 shows the overall plant habit, including blooms, bud and foliage.
Figure 2:
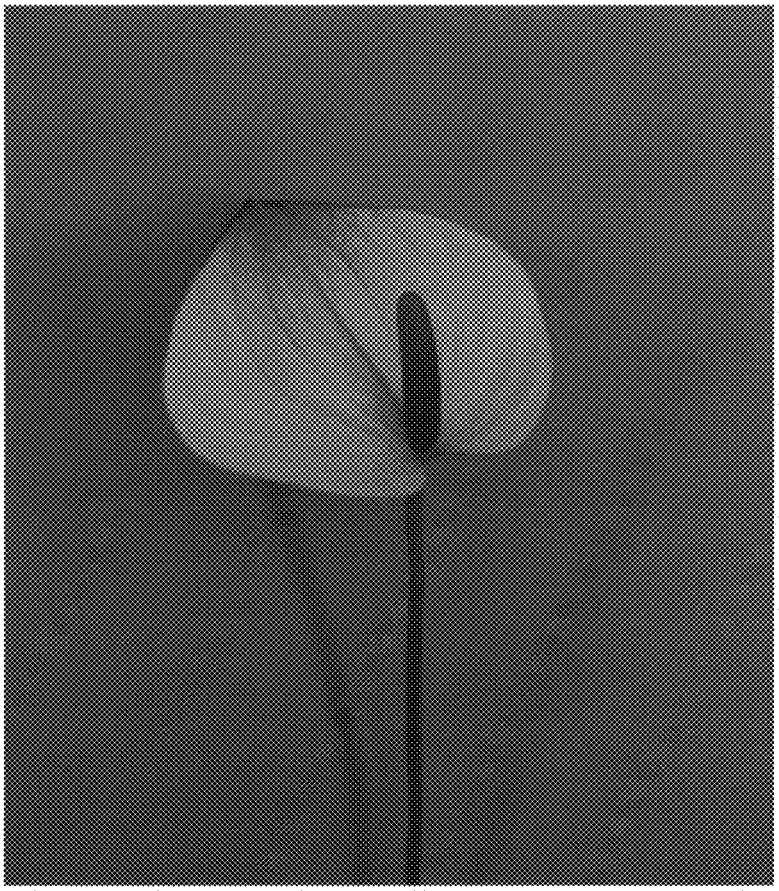
FIG. 2 shows a close-up of the mature spathe.
Figure 3:
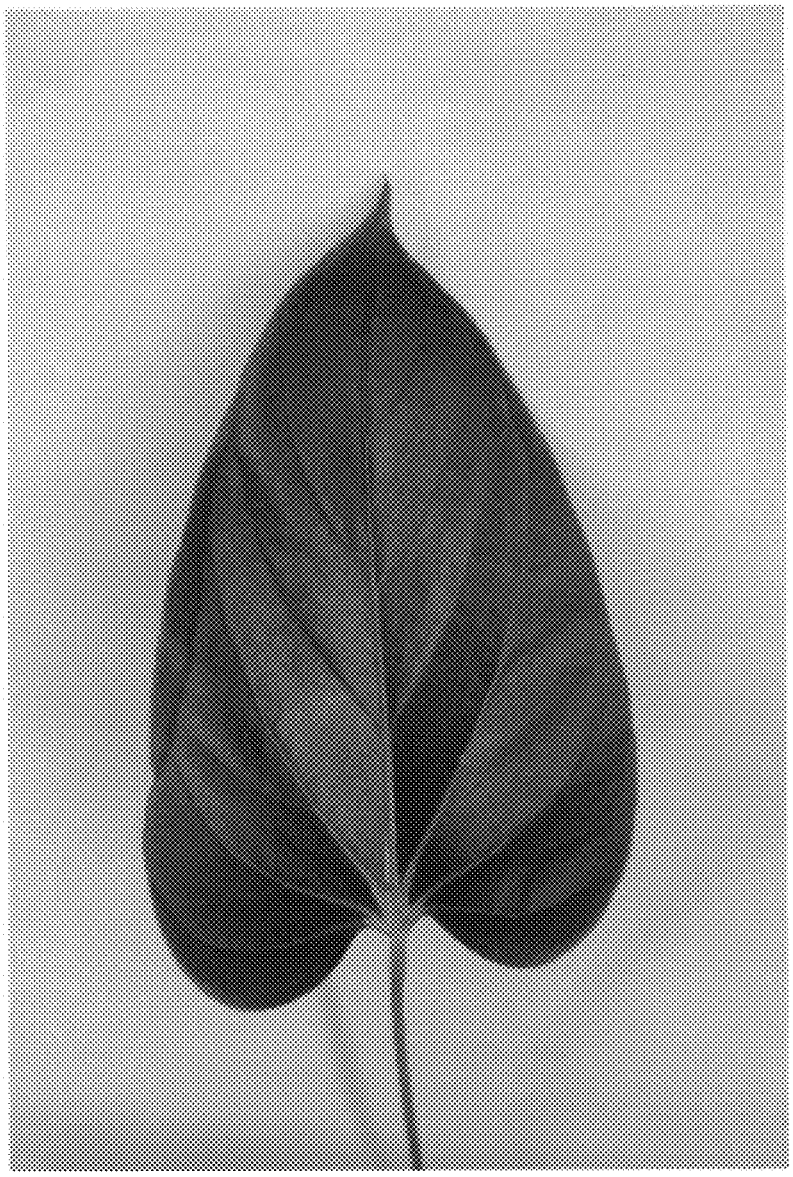
FIG. 3 shows a close-up of the upper leaf blade surface.

The following detailed description sets forth the distinctive characteristics of 'ANTHFAXI'. The data which define these characteristics were collected from asexual reproductions carried out in Bleiswijk, The Netherlands. The plant history was taken on 42 to 46-week old plants which were planted from tissue culture in 14 centimeter (diameter) pots and grown in a glass greenhouse between 19° C. and 24° C. Observations were made in June 2017. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.
*Botanical*.—*Anthurium andraeanum* L.
*Common name*.—*Anthurium*.
*Denomination*.—'ANTHFAXI'.

Parentage:

*Female parent.*—*Anthurium* plant '16542-06' (unpatented).

*Male parent.*—*Anthurium* plant '18376-08' (unpatented).

Plant:

*Propagation.*—Tissue culture.

*Root description.*—Fleshy-creamy (RHS 158A) colored roots with small hairy lateral roots having yellow (RHS 9A) colored root tips.

*Time to produce a finished flowering plant.*—42 to 46 weeks after planting in a 14 cm (diameter) pot.

*Growth habit.*—Herbaceous perennial.

*Height* (*measured from soil, including inflorescence*).—30.0 cm to 35.0 cm.

*Width* (*measured from leaf tips*).—48.0 cm to 52.0 cm.

Leaves:

*Immature leaves.*—Length: 10.0 cm to 12.0 cm. Width: 6.5 cm to 7.5 cm. Color: Upper surface: RHS 146A. Lower surface: RHS 146B. Texture (both upper and lower surfaces): Soft and smooth.

*Mature leaves.*—Length (fully expanded): 16.0 cm to 18.0 cm. Width: 10.0 cm to 12.0 cm. Shape: Ovate-cordate. Apex: Acuminate. Base: Cordate. Leaf blade angle with the petiole: Between 125 degrees and 135 degrees. Leaf margin: Entire. Color: Upper surface: RHS 147A. Lower surface: RHS 147B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes.*—Present. Arrangement: Leaf blade has two lobes extending past the petiole. The lobes are non-touching. Length of lobes of mature leaf blades: 0.5 cm to 1.5 cm. Width of lobes of mature leaf blades: 3.5 cm to 4.5 cm. Distance from petiole/leaf junction to highest point on lobes of mature leaf: 2.0 cm to 4.0 cm.

*Petiole.*—Cross-section: Round. Diameter: 0.3 cm to 0.4 cm. Length: 12.0 cm to 14.0 cm for a mature leaf size. Color: Mature leaf: RHS 144A. Immature leaf: RHS 144B. Cataphyll color surrounding the petiole: Outside: RHS 144B with red tip (RHS 53C). Inside: RHS 144C.

*Geniculum.*—Length: 2.0 cm to 2.5 cm. Width: 0.4 cm to 0.5 cm. Color: RHS 144B.

Inflorescence:

*Arrangement.*—Single.

*Flowering habit* (*length of flowering season*).—Continuous.

*Number of inflorescences per plant.*—4 to 6.

*Fragrance.*—Absent.

*Longevity of inflorescence on plant.*—Over half a year.

Spathe:

*Buds.*—The spathe is tightly rolled around the spadix and extrudes from the peduncle sheath. After the spathe is fully open, the peduncle elongates some extra centimeters.

*Bud length.*—4.5 cm to 5.0 cm.

*Bud diameter.*—0.8 cm to 1.0 cm.

*Bud color.*—RHS 160D at the base; RHS 49B toward the tip and a RHS N45A tip.

*Bud texture.*—Smooth.

*Arrangement.*—Spathe angle with the peduncle is between 90 degrees and 110 degrees; the spathe stands on a wiry peduncle about 3.0 cm to 6.0 cm above the foliage.

*Shape.*—Cordate.

*Apex.*—Mucronate.

*Base.*—Cordate.

*Texture.*—Blistered.

*Blistering.*—Weak.

*Margin.*—Entire.

*Size.*—Length: 7.0 cm to 8.0 cm. Width: 8.0 cm to 8.5 cm.

*Lobes.*—Present.

*Arrangement.*—The spathe has two lobes extending past the peduncle. The lobes are non-touching. Length: 0.5 cm to 1.0 cm. Width: 2.5 cm to 3.0 cm.

*Color.*—Just fully open: Upper surface: White (RHS 155C) with red tip (RHS 46A) and lighter red region (RHS 46B) toward the spadix. Lower surface: White (RHS 155C) with red region (RHS 47B) toward the tip. This white color with red tip remains for a very long period, at least more than 25 weeks after opening.

Peduncle:

*Shape.*—Erect.

*Cross-section.*—Round.

*Length.*—24.0 cm to 27.0 cm.

*Diameter.*—0.3 cm to 0.4 cm.

*Color.*—RHS 144B.

Flowering time:

*General.*—One small, rooted, untreated tissue culture plant of 8.0 cm tall will flower, depending on season, after 42 to 46 weeks and 4 to 5 blossoms appear. More blossoms appear after some additional weeks so that a full flowering and commercial plant will have 5 to 6 white spathes with red tips. Smaller blossoms may occur on immature plants.

Spadix:

*Size.*—Length: 3.0 cm to 4.0 cm (depending on flower size). Width (at apex): 0.5 cm to 0.6 cm. Width (at base): 0.6 cm to 0.7 cm.

*Shape.*—Columnar.

*Angle from spadix tip to peduncle.*—170 degrees to 180 degrees.

*Curvature of the longitudinal axis.*—Straight.

*Texture.*—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color.*—Immature: RHS 45A. Mature: RHS 53A. Ages to: RHS 53A.

Flowers:

*Quantity per spadix.*—90 to 120.

*Spadix flower arrangement.*—Bisexual, rounded in cross-section.

*Shape.*—Rounded.

*Size.*—Length: 0.05 cm to 0.10 cm. Diameter (maximum): 0.10 cm.

*Color.*—RHS 54D.

Reproductive organs:

*Stamens.*—Not visible.

*Pollen amount.*—Absent.

*Pistil*.—Quantity: 90 to 120. Length: Less than 0.01 cm. Color: RHS 54D.

*Style*.—Not observed.

*Stigma*.—Shape: Ovoid. Diameter: Less than 0.01 cm. Color: RHS 54D.

*Ovary*.—Rarely visible.

*Ovary color*.—Not measured.

Fruit and seed set: None observed.

Disease and pest resistance: No specific resistance or susceptibility observed to pathogens and pests common to *Anthurium* under commercial conditions.

COMPARISON WITH PARENTAL AND COMMERCIAL VARIETIES

'ANTHFAXI' differs from the female parent plant '16542-06' (unpatented) in that 'ANTHFAXI' has a red (RHS 45A) immature spadix that matures to RHS 53A, whereas '16542-06' has a red (RHS 42B) immature spadix that matures to RHS 51B. Additionally, 'ANTHFAXI' has shorter spadix than '16542-06'.

'ANTHFAXI' differs from the male parent plant '18376-08' (unpatented) in that 'ANTHFAXI' has shorter spadix and spathes with a smaller diameter than '18376-08'.

'ANTHFAXI' differs from similar commercial variety 'ANTHFOFUN' (unpatented) in that 'ANTHFAXI' has white spathes with red, mucronate shaped tips that are lighter red toward the spadix, whereas 'ANTHFOFUN' has light pink spathes with abruptly acuminate shaped tips and green lobes. Additionally, 'ANTHFAXI' has longer leaves than 'ANTHFOFUN'.

'ANTHFAXI' differs from similar commercial variety 'ANTHCONAP' (unpatented) in that 'ANTHFAXI' has white, cordate shaped spathes with red tips that are lighter red toward the spadix and non-touching lobes, whereas 'ANTHCONAP' has red, oblong-cordate shaped spathes with green, overlapping lobes. Additionally, 'ANTHFAXI' is a smaller plant with shorter leaves than 'ANTHCONAP'.

I claim:

1. A new and distinct variety of *Anthurium* plant named 'ANTHFAXI', substantially as illustrated and described herein.

* * * * *